(12) United States Patent
Nakamura

(10) Patent No.: US 8,488,239 B2
(45) Date of Patent: Jul. 16, 2013

(54) MEDICAL STAND DEVICE, MEDICAL MICROSCOPE, AND EXTERNAL ILLUMINATING DEVICE

(75) Inventor: Katsushige Nakamura, Tokyo (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 333 days.

(21) Appl. No.: 12/746,263

(22) PCT Filed: Dec. 5, 2008

(86) PCT No.: PCT/JP2008/072202
§ 371 (c)(1),
(2), (4) Date: Jun. 4, 2010

(87) PCT Pub. No.: WO2009/072630
PCT Pub. Date: Jun. 11, 2009

(65) Prior Publication Data
US 2010/0271697 A1    Oct. 28, 2010

(30) Foreign Application Priority Data

Dec. 7, 2007  (JP) .................... 2007-317525
Dec. 7, 2007  (JP) .................... 2007-317532
Dec. 7, 2007  (JP) .................... 2007-317535
Dec. 7, 2007  (JP) .................... 2007-317540

(51) Int. Cl.
*G02B 21/06* (2006.01)

(52) U.S. Cl.
USPC ................ 359/385; 359/388; 359/390

(58) Field of Classification Search
USPC .................................... 359/385–390
See application file for complete search history.

(56) References Cited

U.S. PATENT DOCUMENTS

| | | | |
|---|---|---|---|
| 5,973,829 A | 10/1999 | Moller et al. | |
| 6,398,721 B1 | 6/2002 | Nakamura et al. | |
| 7,580,185 B2 * | 8/2009 | Haisch et al. | 359/385 |
| 2002/0109912 A1 * | 8/2002 | Knoblich | 359/385 |
| 2003/0184712 A1 * | 10/2003 | Takeda et al. | 351/245 |
| 2004/0109231 A1 | 6/2004 | Haisch et al. | |
| 2005/0018280 A1 * | 1/2005 | Richardson | 359/368 |
| 2007/0070294 A1 | 3/2007 | Kim | |
| 2008/0013166 A1 * | 1/2008 | Haisch et al. | 359/353 |

FOREIGN PATENT DOCUMENTS

| | | |
|---|---|---|
| JP | 04144554 | 5/1992 |
| JP | 06114009 A | 4/1994 |
| JP | 08173389 A | 7/1996 |

(Continued)

OTHER PUBLICATIONS

International Search Report, PCT/JP2008/072202 (2 pages).

(Continued)

*Primary Examiner* — Frank Font
(74) *Attorney, Agent, or Firm* — Edell, Shapiro & Finnan, LLC

(57) ABSTRACT

An optical filter 11 is fixed in an optical path in a light generation unit 6 to cut out light in an infrared region. The optical filter 11 do not deviate from the optical path, and infallibly eliminate light in the infrared region which becomes heat radiation. The optical filter 11 cuts out light whose wavelength is longer than a threshold wavelength that is longer than 805 nm and shorter than 815 nm, and eliminates heat radiation in the infrared region, which includes a wavelength (approximately 825 nm) which is substantially a first peak P of the radiant intensity of the xenon lamp 10.

6 Claims, 17 Drawing Sheets

FOREIGN PATENT DOCUMENTS

| | | |
|---|---|---|
| JP | 09135814 A | 5/1997 |
| JP | 10201707 | 8/1998 |
| JP | 11137567 A | 5/1999 |
| JP | 2000097859 | 4/2000 |
| JP | 2001208978 A | 8/2001 |
| JP | 2004163413 A | 6/2004 |
| JP | 2004222938 A | 8/2004 |
| JP | 2005185304 A | 7/2005 |
| JP | 2007534428 A | 11/2007 |

OTHER PUBLICATIONS

International Preliminary Report on Patentability and Written Opinion, PCT/JP2008/072202 (6 pages).

Japanese Office Action, Feb. 5, 2013, 3 pages.

* cited by examiner

MEDICAL STAND DEVICE, MEDICAL MICROSCOPE, AND EXTERNAL ILLUMINATING DEVICE

TECHNICAL FIELD

The present invention relates to a medical stand device, a medical microscope and an external illuminating device, and particularly to a medical stand device, a medical microscope and an external illuminating device which prevent an affected area from being heated by illumination light.

BACKGROUND ART

In the modern medicine, knowledge has been disseminated on a technology in which: a fluorescent substance is administered to a patient; when the fluorescent substance is accumulated in an affected area to a certain amount, the affected area is irradiated with an excitation light whose wavelength can excite the fluorescent substance; thereby, fluorescent light is emitted only from the affected area; and thus, fluorescence observation and fluorescence photography are applied to the affected area by use of an optical filter which transmits only the fluorescent light.

5-aminolevulinic acid (5-ALA), talaporfin sodium (whose registered trademark is Laserphyrin), indocyanine green (ICG) and the like are known as fluorescent substances. 5-aminolevulinic acid emits fluorescent light with a wavelength of approximately 620 nm when receiving excitation light with a wavelength of approximately 380 nm. Talaporfin sodium emits fluorescent light with a wavelength of approximately 672 nm when receiving excitation light with a wavelength of approximately 664 nm. Indocyanine green emits fluorescent light with a wavelength of approximately 835 nm when receiving excitation light with a wavelength of approximately 805 nm. Indocyanine green is the closest to infrared light.

The above excitation light is also used as illumination light for a microscope which observes the affected area. In other words, illumination light for observing the affected area with the microscope is irradiated on the affected area from the beginning, and the illumination light is used as the excitation light. The microscope is supported by an arm of a stand device, and an irradiation hole is formed in the bottom surface of the microscope. The illumination light is supplied to the microscope from a light generating unit through an optical fiber, and is thus irradiated onto the affected area from the irradiation hole of the microscope. The light generating unit is installed inside or outside the main body of the stand device. A xenon lamp or a halogen lamp being capable of emitting white light close to solar light and having good color rendering properties is generally used as a source of light used in the light generating unit.

The light generating unit is provided with: a thermally-protective optical filter configured to cut wavelengths in the infrared region, which become heat radiation on the affected area, from the illumination light; and a fluorescence filter configured to selectively transmit only excitation light, whose wavelength corresponds to the fluorescent substance, from the illumination light from the source of light. One of these two optical filters selectively intervenes in the optical path of the illumination light from the source of light while sliding or revolving into the optical path. Usually, the thermally-protective optical filter intervenes in the optical path, and thereby transmits visible light and cuts infrared light. During a fluorescence observation, the fluorescence optical filter intervenes in the optical path, and thus selectively transmits only excitation light whose wavelength corresponds to the fluorescent substance (see Patent Document 1).

[Patent Document 1] Japanese Patent Application No. 2004-163413.

DISCLOSURE OF INVENTION

Technical Problem

In such prior art, however, the thermally-protective optical filter and the fluorescence optical filter are moved by an actuator. As a result, when the actuator or the like is out of order, both the filters may deviate from the optical path of the illumination light inside the light generating unit; and the illumination light from the source of light may be irradiated on the affected area in a full output mode. For this reason, a sensor for detecting positional deviations of the optical filters needs to be installed inside the light generating unit. This installation complicates the structure of the light generating unit.

The present invention has been made with such prior art taken into consideration. The present invention provides a medical stand device, a medical microscope and an external illuminating device: which are capable of irradiating excitation light which corresponds to various fluorescent substances; and which eliminates heat radiation included in illumination light.

Technical Solution

A first aspect of the present invention is a medical stand device including: an arm configured to support a microscope; a stand main body configured to support the arm; a light generating unit installed inside the stand main body, the light generating unit being configured to generate illumination light which is supplied to the microscope; and optical means configured to cut out part of the illumination light whose wavelength is longer than a threshold wavelength that is longer than 805 nm and shorter than 815 nm, wherein the light generating unit includes any one of a xenon lamp and a halogen lamp as a light source, and the optical means is fixed on an optical path of the illumination light from the light generating unit to the microscope.

A second aspect of the present invention is a medical microscope including: a microscope main body; an internal optical path provided in the microscope main body, and configured to transmit illumination light introduced from an outside; an irradiation hole formed in a bottom surface of the microscope main body, the illumination light going out of the irradiation hole after passing the internal optical path; and optical means configured to cut out part of the illumination light whose wavelength is longer than a threshold wavelength that is longer 805 nm and shorter 815 nm, wherein the optical means is fixed to any one of the internal optical path and the irradiation hole.

It is preferable that the medical microscope further include: an arm configured to support the microscope main body; a stand main body configured to support the arm; and a light generating unit installed inside the stand main body, and configured to generate the illumination light and to supply the illumination light to the microscope main body, wherein the light generating unit includes any one of a xenon lamp and a halogen lamp as a light source.

A third aspect of the present invention is an external illuminating device configured to illuminate an affected area through an irradiation hole of a medical microscope, the affected area being to be observed by use of the medical microscope, including: a light source for the illumination light; a housing configured to house the light source; optical means configured to cut out part of the illumination light, whose wavelength is longer than a threshold wavelength that is longer than 805 nm and shorter than 815 nm, wherein the light source is any one of a xenon lamp and a halogen lamp, and the optical means is placed in an optical path of the illumination light inside the housing.

In the first to third aspects of the present invention, it is preferable that the optical means is any one of a transmitting optical filter and a reflecting optical filter.

Advantageous Effects

According to the present invention, the optical means fixed on the optical path of the illumination light always cuts out light in an infrared region from the illumination light. Because the optical means do not deviates from the optical path, light in the infrared region, which becomes heat radiation, can be infallibly eliminated.

BEST MODES FOR CARRYING OUT THE INVENTION

Figure 1:
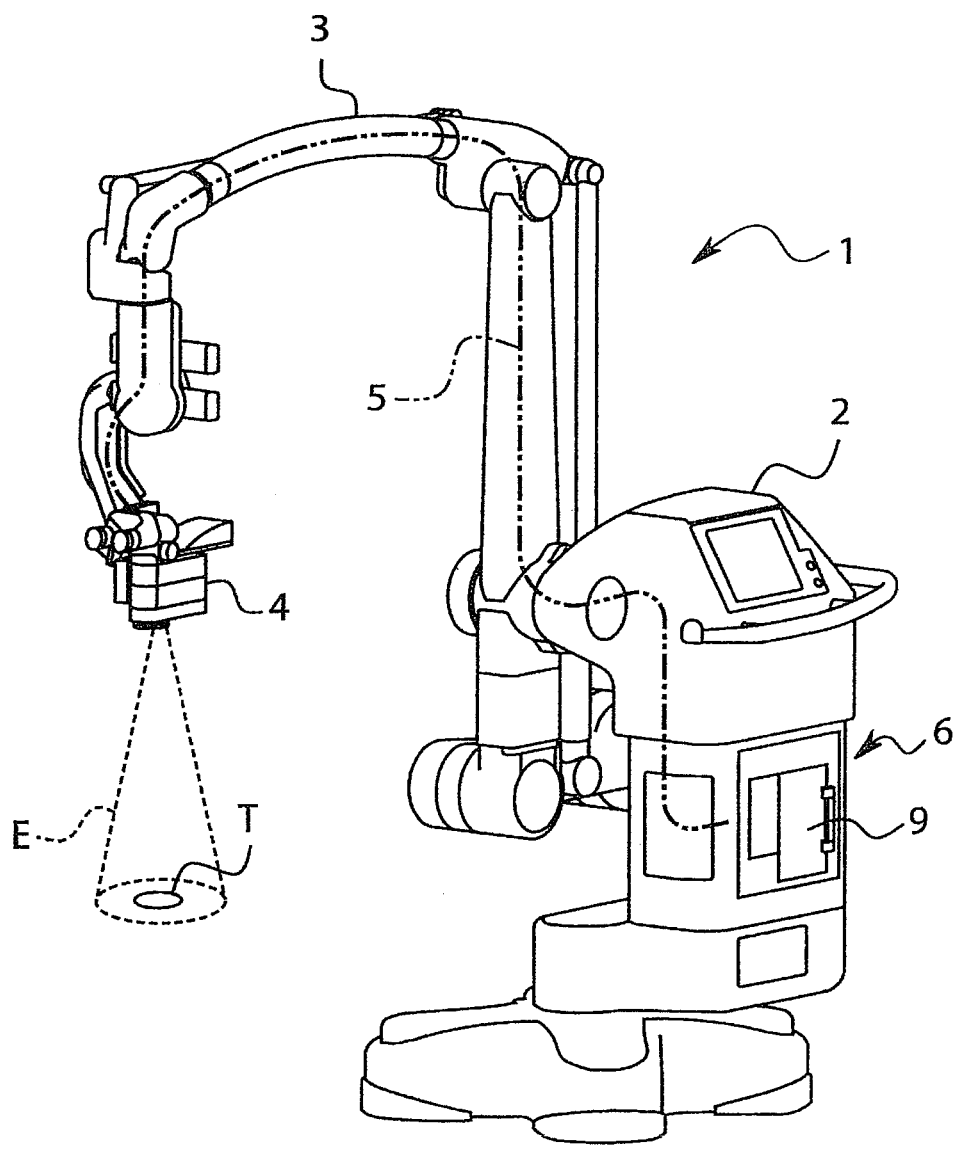
FIG. 1 is an overall perspective view showing a stand device according to a first embodiment of the present invention.
Figure 2:
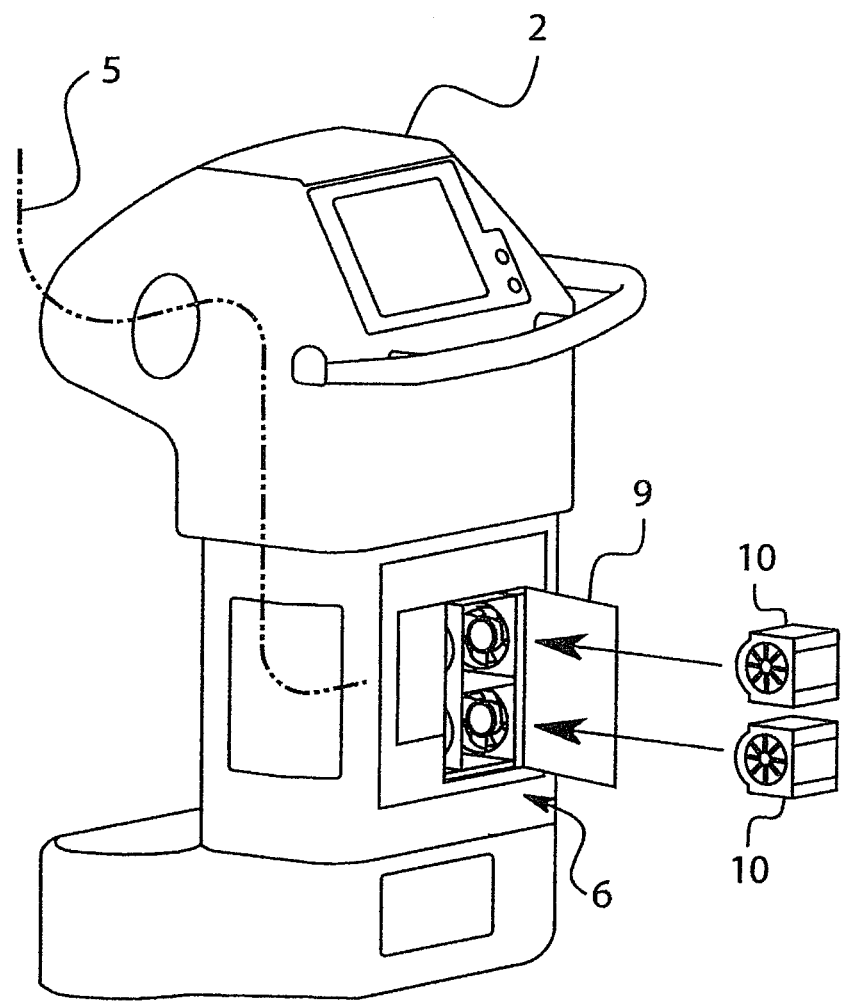
FIG. 2 is a perspective view showing a stand main body according to the first embodiment.
Figure 3:
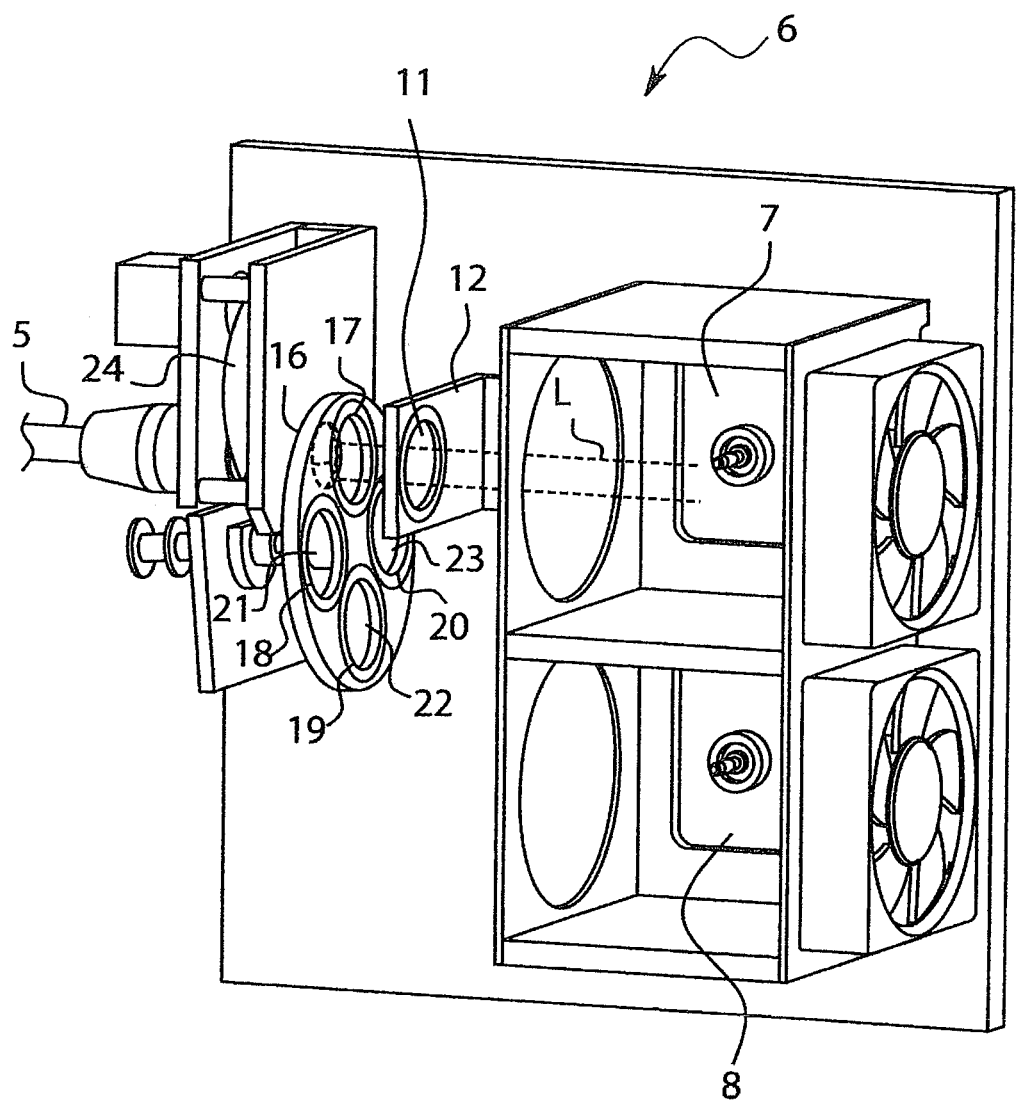
FIG. 3 is a perspective view showing a light generating unit inside the stand main body.
Figure 4:
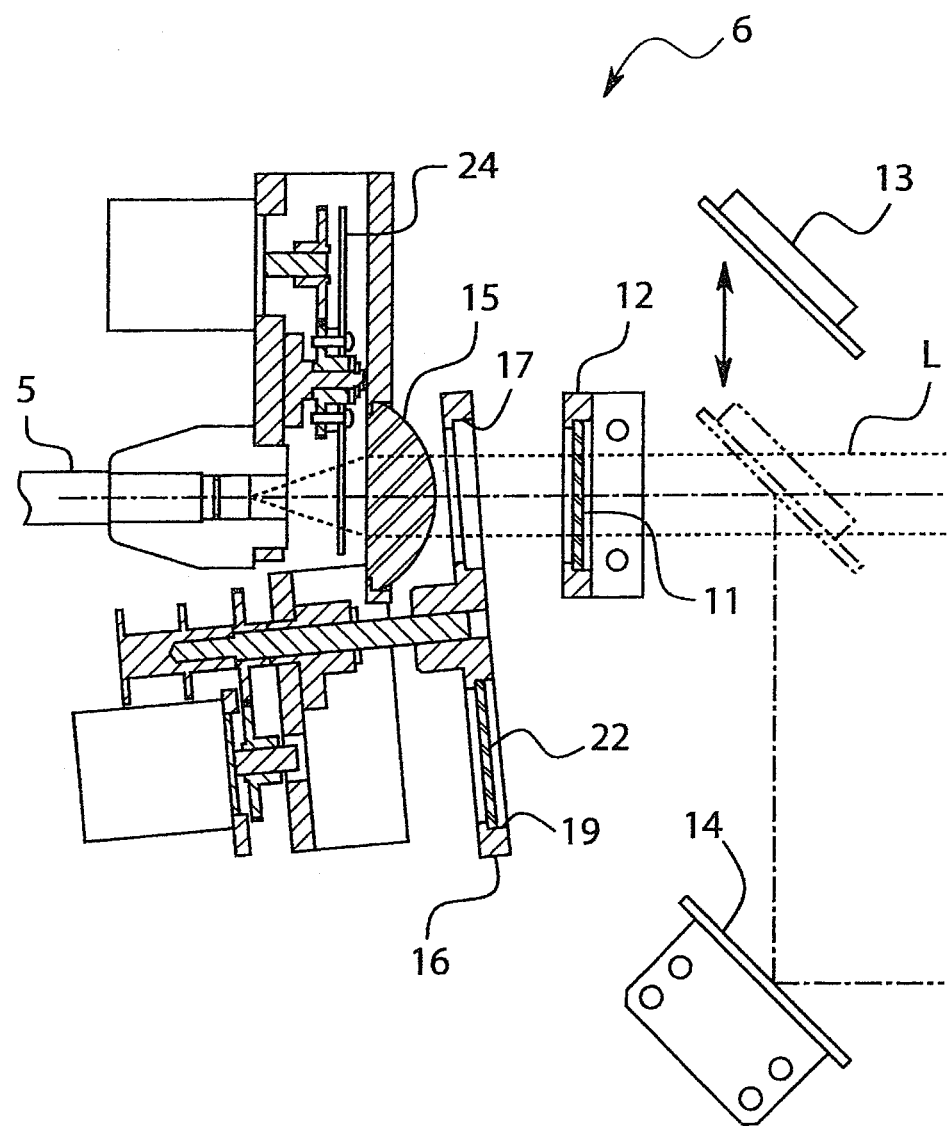
FIG. 4 is a cross-sectional view showing a main section of the light generating unit according to the first embodiment.
Figure 5:
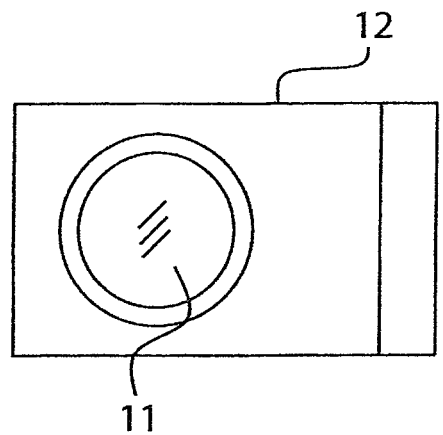
FIG. 5 is a schematic view showing an optical filter according to the first embodiment.
Figure 6:
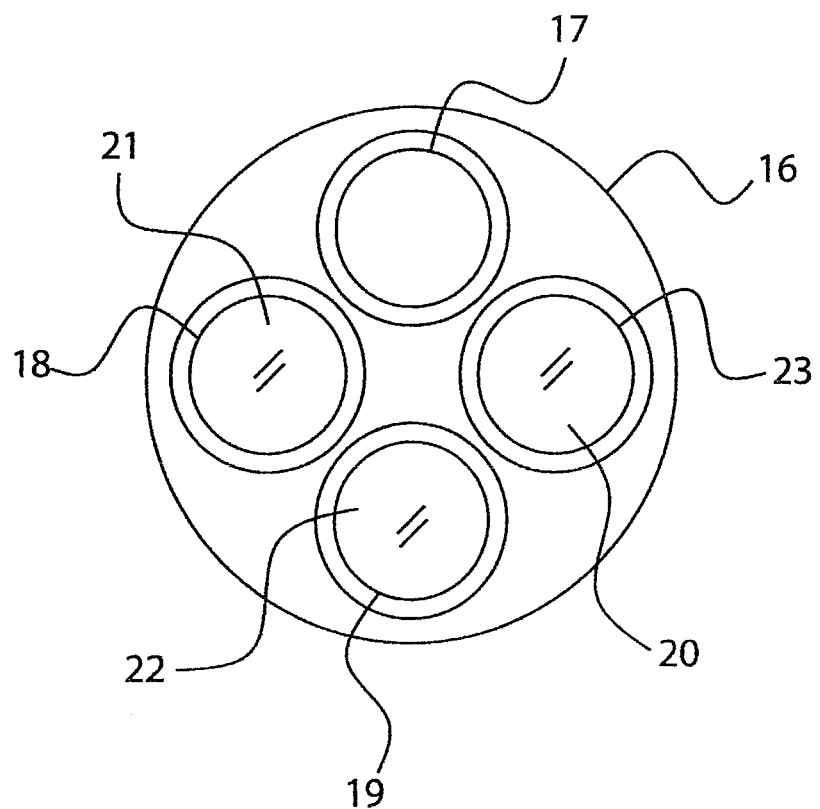
FIG. 6 is a schematic view showing a rotary plate according to the first embodiment.
Figure 7:
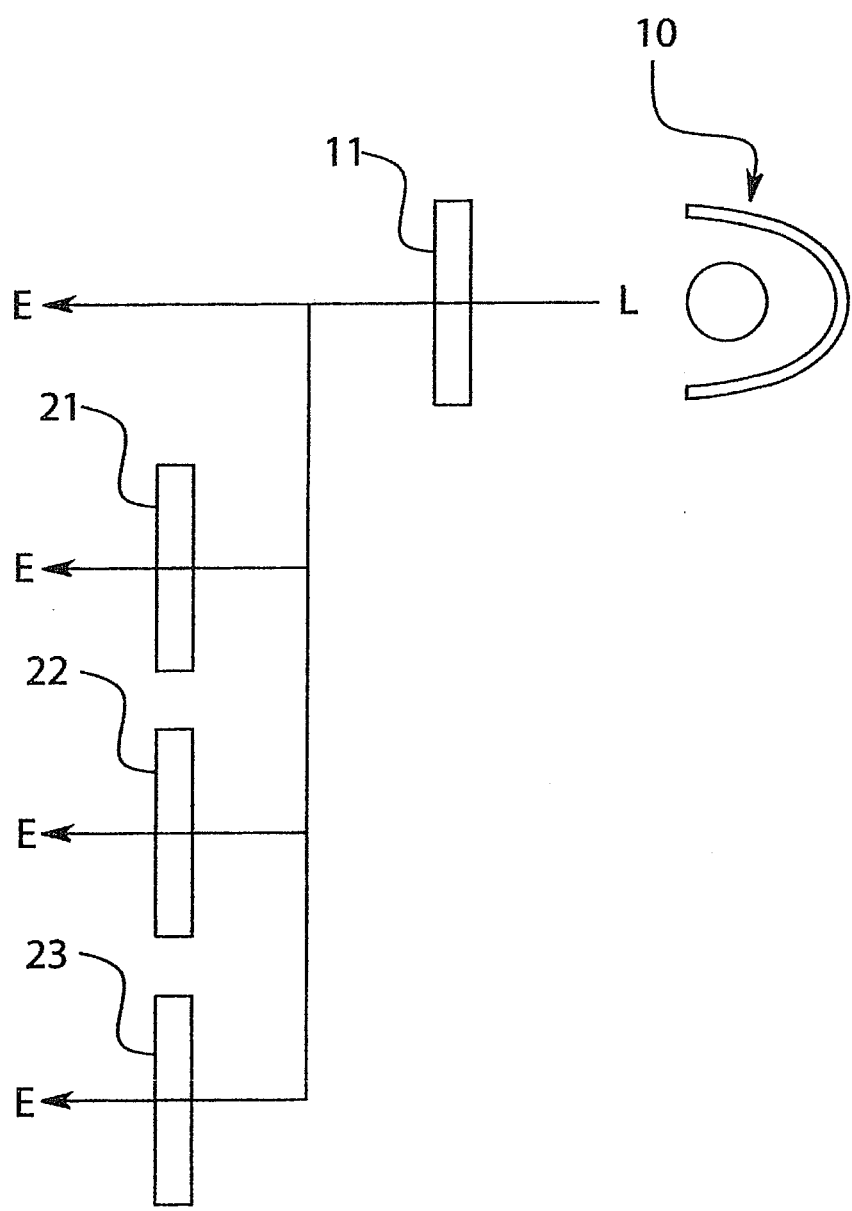
FIG. 7 is an explanatory diagram showing how different types of excitation filters respectively transmit only a necessary wavelength component.

Descriptions will be provided for preferable embodiments of the present invention.

(First Embodiment)

FIGS. 1 to 10 are diagrams showing a first embodiment of the present invention. A stand device 1 includes a main body 2 and an arm 3. A microscope 4 for a surgical operation is supported in a front end of the arm 3 in a well-balance manner.

The arm 3 has a hollow structure. An optical fiber 5 is laid inside of the arm 3. An end of the optical fiber 5 is connected to the microscope 4 in a way that excitation light E, which will be described later, can be irradiated onto an affected area T from an irradiation hole (not illustrated), which is formed in the bottom surface of the microscope 4, after passing in an internal optical path of the microscope 4.

A light generating unit 6 is formed inside the main body 2 of the stand device 1. The light generating unit 6 includes a main lamp storage 7 and a spare lamp storage 8 which are arranged vertically. Thus, when a door 9 of the main body 2 is opened, xenon lamps 10 can be stored in the respective storages 7, 8.

A transmitting optical filter (optical means) 11 is fixed in front of the main lamp storage 7 by a fixation plate 12. It is desirable that the transmitting optical filter 12 be a single optical filter. In this case, since only a single fixed filter is fixed, an existing interstitial space in the light generating unit 6 can be used to install the filter.

A movable mirror 13 is installed in a higher location between the main lamp storage 7 and the optical filter 11. A fixed mirror 14 is installed in front of the spare lamp storage 8. The movable mirror 13 and the fixed mirror 14 are configured as follow. When the xenon lamp 10 in the main lamp storage 7 fails, the xenon lamp 10 in the spare lamp storage 8 is switched on, and the movable mirror 13 descends. Illumination light L from the xenon lamp 10 in the spare lamp storage 8 situated in a lower location is reflected upward by the fixed mirror 14. Thereafter, the reflected illumination light is guided to the original optical path by the movable mirror 13 which has descended.

A condenser lens 15 is installed in front of the optical filter 11. The other end of the optical fiber 5 is fixed to a light-collecting point of the condenser lens 15. A rotary plate 16 is installed between the optical filter 11 and the condenser lens 15. Four holes 17 to 20 are formed in the rotary plate 16. One hole 17 is open. An excitation filter 21, a second excitation filter 22 and a third excitation filter 23 are respectively provided to the three other holes 18, 19, 20. The first to third excitation filters 21 to 23 are bandpass filters which selectively transmit light having necessary wavelengths, respectively, depending on the fluorescent substance. A light intensity controlling filter 24 is installed between the optical fiber 5 and the condenser lens 15. The light intensity controlling filter 24 has a disc shape, and can continuously control a light intensity in a non-step manner by rotating itself.

Figure 8:
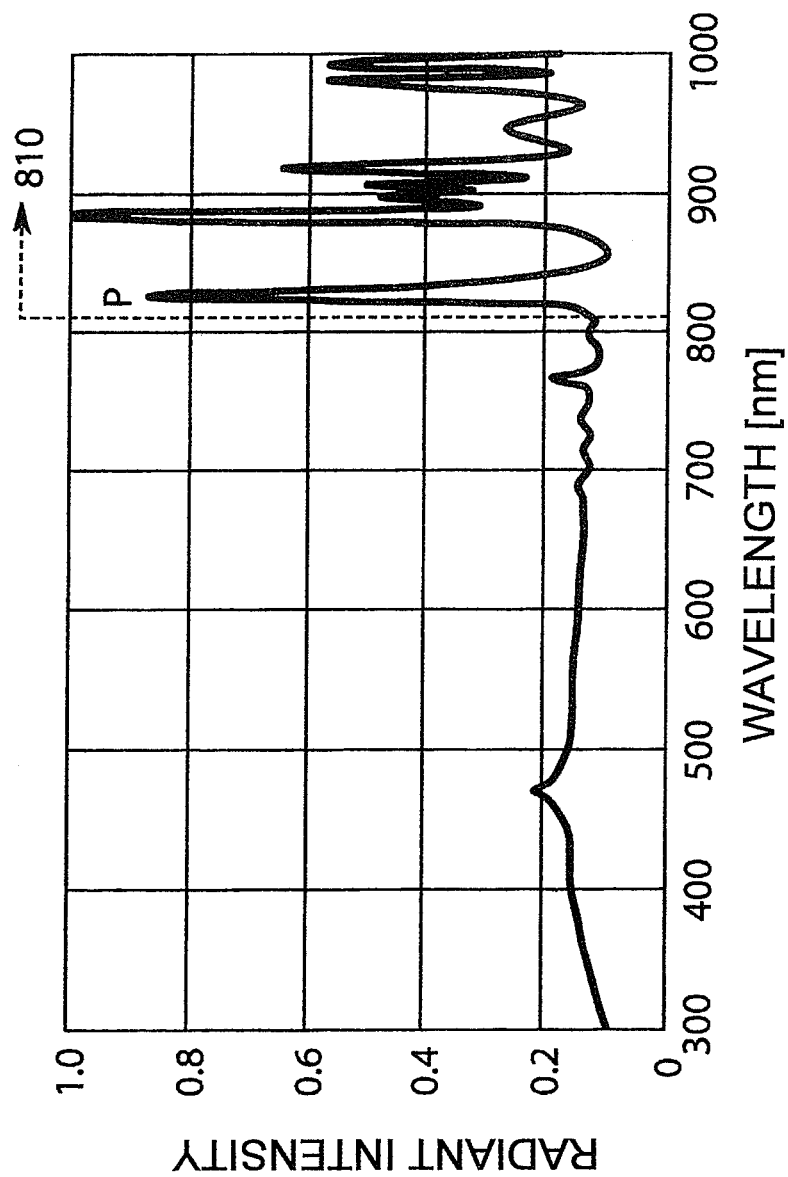
FIG. 8 is a graph showing a radiation spectrum of a xenon lamp.

Next, descriptions will be provided for how the first embodiment operates when indocyanine green is used as a fluorescent substance. The xenon lamp 10 irradiates illumination light L, which has a radiation spectrum as shown in FIG. 8, as parallel rays. A threshold value of the fixed optical filter 11 is set at 810 nm, as clear from FIGS. 9 and 10 (magnifying a main part of FIG. 8). Thus, the fixed optical filter 11 has a characteristic of cutting out light having all the infrared wavelengths, which are longer than 810 nm, from the illumination light L. When indocyanine green is used, the hole 17 penetrating the rotary plate 16 is positioned by revolving in order to face to the optical filter 11.

Figure 10:
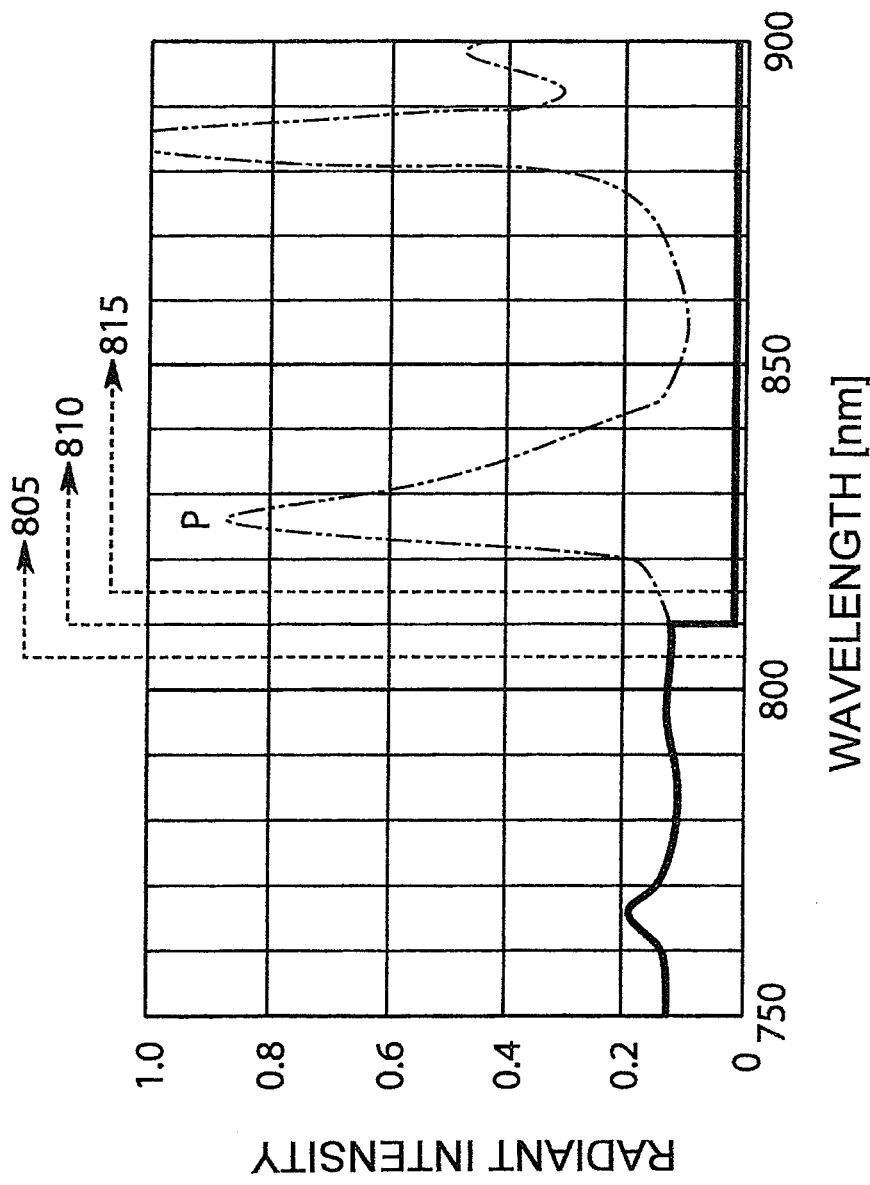
FIG. 10 is a graph corresponding to FIG. 9, and the graph shows a radiation spectrum when the optical filter cuts light whose wavelength is longer than 810 nm.
Figure 11:
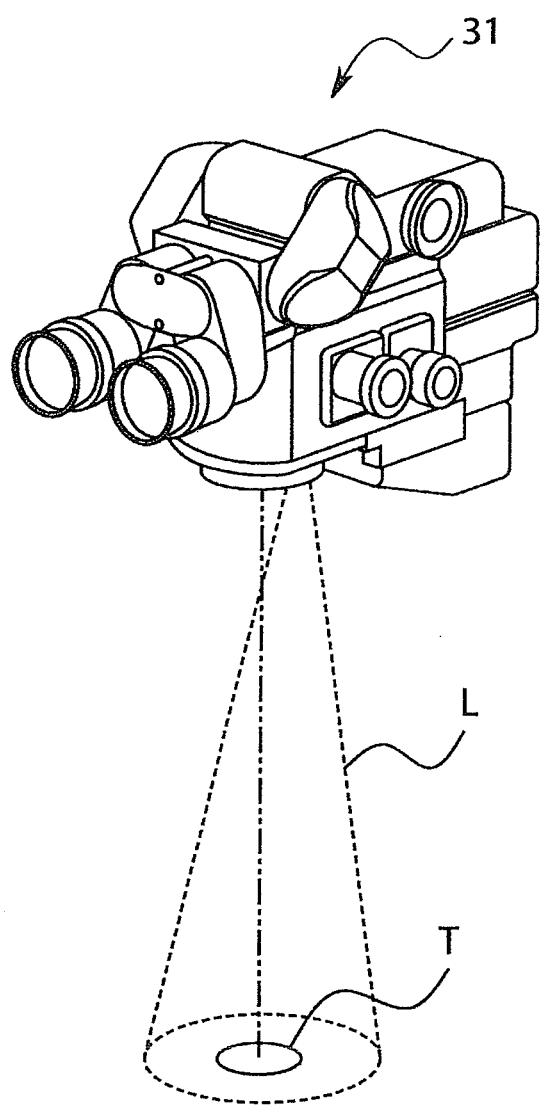
FIG. 11 is an overall perspective view showing a microscope according to a second embodiment of the present invention.
Figure 12:
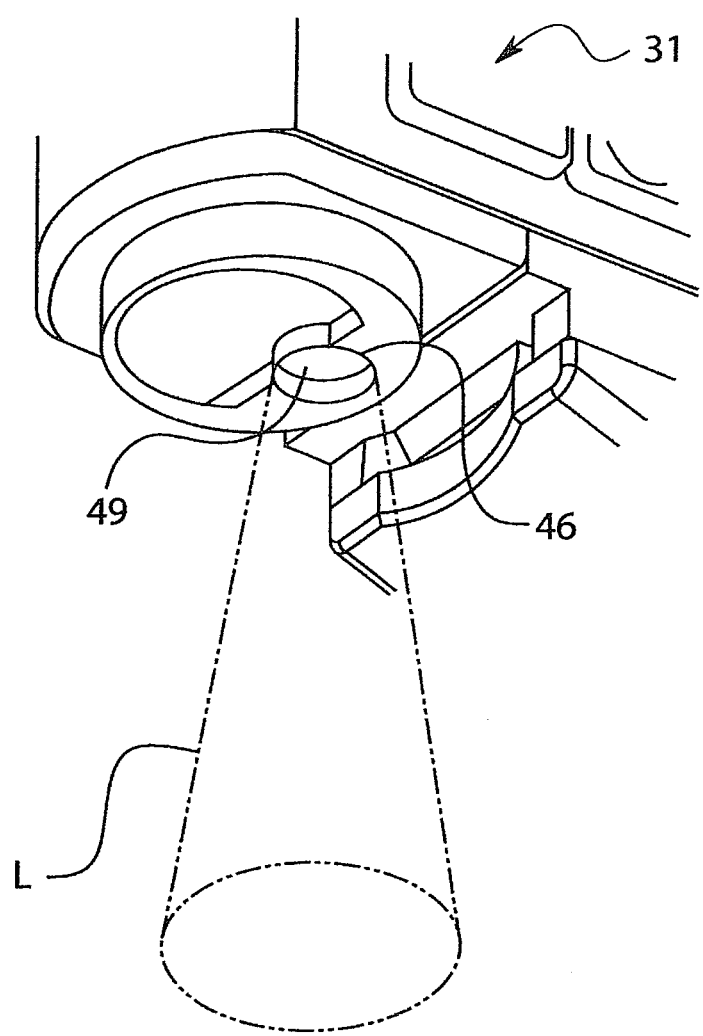
FIG. 12 is a perspective view showing a bottom surface of the microscope according to the second embodiment.
Figure 13:
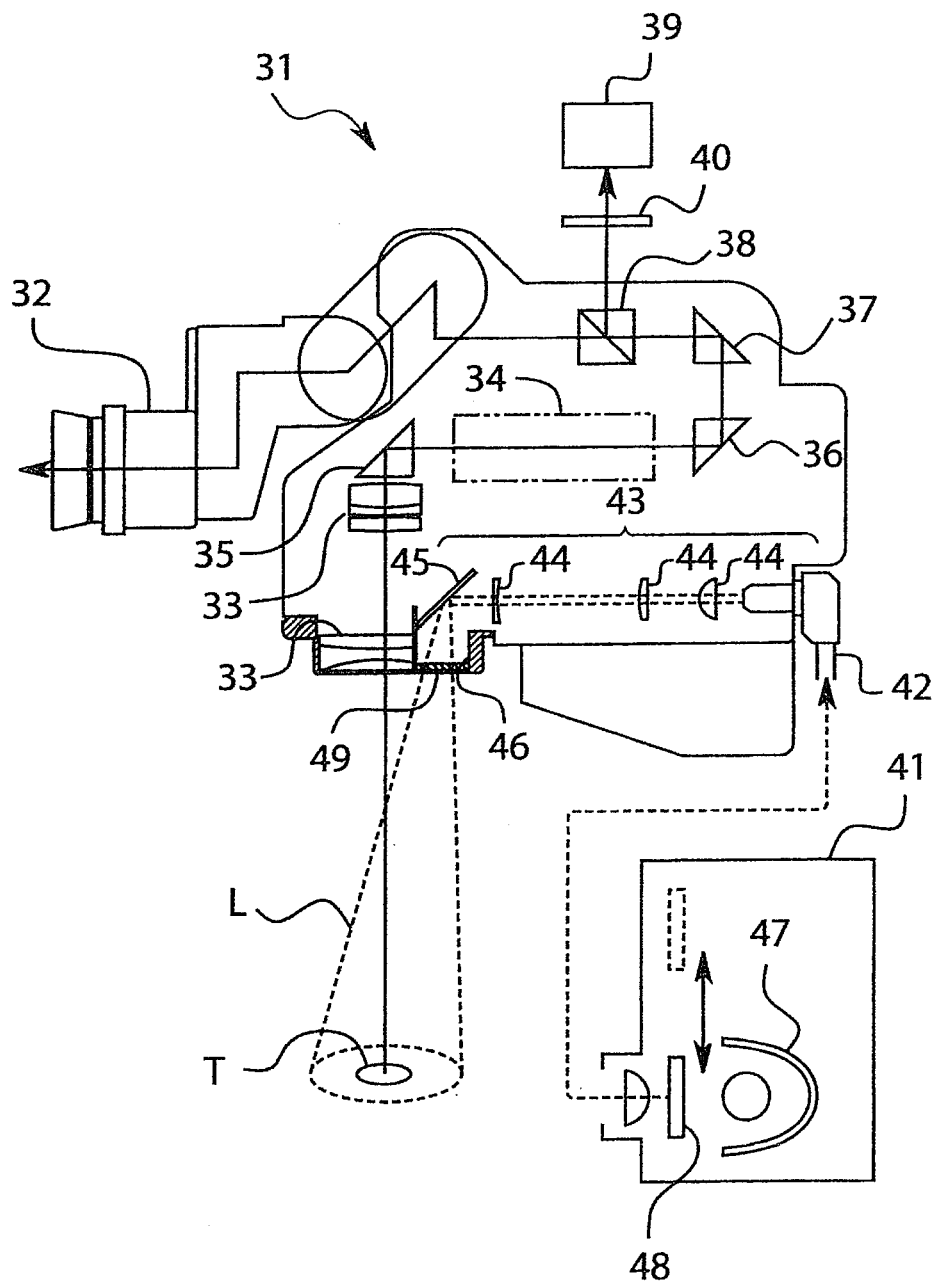
FIG. 13 is a schematic diagram showing an internal configuration of the microscope according to the second embodiment.
Figure 14:
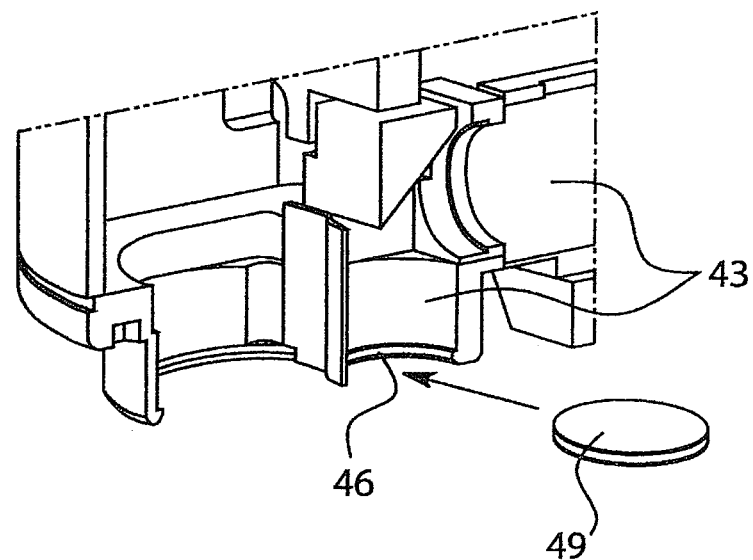
FIG. 14 is a partially cut-away perspective view showing an irradiation hole and its vicinity in the microscope according to the second embodiment.
Figure 15:
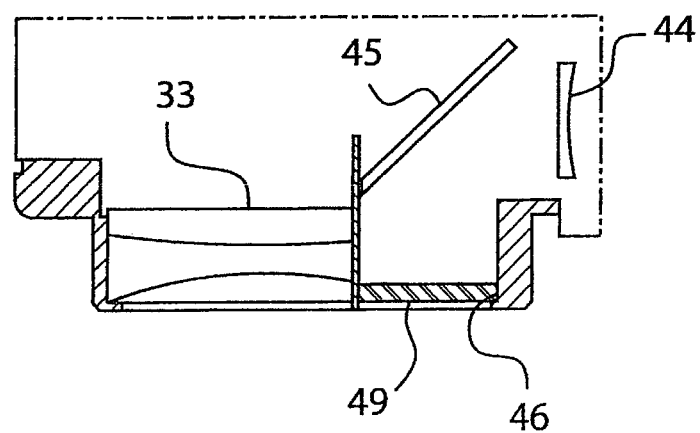
FIG. 15 is a cross-sectional view showing the irradiation hole and its vicinity in the microscope according to the second embodiment.

Accordingly, as shown in FIG. 10, the illumination light L from the xenon lamp 10 turns into excitation light E from which all the infrared wavelengths longer than 810 nm are cut. The excitation light E passes the hole 17 penetrating the rotary plate 16, and is condensed by the condenser lens 15. Thereafter, the light intensity of the condensed excitation light E is appropriately controlled by the light intensity controlling filter 24, and the resultant excitation light E is introduced into the other end of the optical fiber.

The excitation light E, which has been introduced into the other end of the optical fiber 5, is guided to the microscope 4 through the optical fiber 5, and is thus irradiated onto the affected area T from the bottom surface of the microscope 4.

As a fluorescent substance, indocyanine green is beforehand accumulated in the affected area T. The excitation light E, which includes an 805-nm wavelength for exciting indocyanine green, causes indocyanine green to emit fluorescent light from the affected area T. The affected area T, which is emitting the fluorescent light, can be observed (photographed) by use of the microscope 4 through a filter (not illustrated) which transmits only the fluorescent wavelength.

The affected area T is irradiated with the excitation light E. However, the affected area T is not overheated because the excitation light E does not include wavelengths in an infrared region which are longer than 810 nm, and which accordingly become heat radiation. Particularly, heat radiation is infallibly eliminated from the illumination light from the xenon lamp 10 by cutting out the infrared region beyond a wavelength (810 nm) shorter than approximately 825 nm which is substantially a first peak P of a radiant intensity of the xenon lamp 10. Note that, because this excitation light E includes visible light, the excitation light E can be also used for a normal observation other than the fluorescence observation.

When a fluorescent substance other than indocyanine green is used, light at a wavelength needed to excite the fluorescent substance may be selectively transmitted by use of a corresponding one of the first to third excitation filters 21, 22, 23, which is other than the optical filter 11, in the rotary plate 16. In this case, the optical filter 11 can infallibly deal with 5-aminolevulinic acid and talaporfin sodium whose excitation wavelengths are shorter than that of indocyanine green, no matter which type of excitation filter may be selected, or whether or not any one of the excitation filters may be selected. That is because the optical filter 11 has the characteristic in which the optical filter 11 is capable of dealing with even indocyanine green whose excitation wavelength is the closest to the infrared wavelengths.

When any other fluorescent substance is used, heat radiation components can be infallibly eliminated from the illumination light L from the xenon lamp 10 because of fixed installation of the optical filter 11 to cut out the infrared region beyond a wavelength shorter than the wavelength which is the first peak P of the radiant intensity of the xenon lamp 10. In other words, no heat radiation is irradiated onto the affected area T irrespective of a type of excitation filter or the presence or absence of the excitation filter. This is because the optical filter 11 is always fixed on the optical path of the illumination light from the xenon lamp 10 to the microscope 4, and thus is placed in order to cut out the heat radiation component from the illumination flux. Furthermore, it is desirable that the location to which the optical filter 11 is fixed be closer to the xenon lamp 10 than to the light intensity controlling filter 24.

In the foregoing embodiment, the transmitting optical filter 11 has been shown as an instance of the optical means. However, a reflecting optical filter, a combination of the transmitting optical filter and the reflecting optical filter, or any other optical means may be used.

Instead of the xenon lamp, a halogen lamp capable of exciting the above-mentioned fluorescent substances may be used as the source of light for the illumination light L. Although illumination light from the halogen lamp includes infrared light, such infrared light is always cut out by the optical filter 11 as well. For this reason, it is possible to prevent the affected area from being heated.

(Second Embodiment)

FIGS. 11 to 15 are diagrams showing a second embodiment of the present invention. A microscope 31 for a surgical operation is supported by an arm of a stand device, which is not illustrated, inside an operating room. The microscope 31 is a stereomicroscope including two eyepiece units 32. Inside the microscope 31, focus lenses 33 is perpendicularly installed, and a zoom lens 34 is horizontally installed.

Light having passed the focus lenses 33 is guided to the zoom lens 34 through a prism 35. Light having passed the zoom lens 34 is redirected to the eyepiece units 32 side through two prisms 36, 37. A beam splitter 38 configured to split part of light is installed between the prism 37 and the eyepiece units 32. Thus, an image represented by the split part of light can be taken by an area camera (hereinafter referred to as a "CCD camera") 39 which uses an image sensor such as a Charge-Coupled Device. A filter 40 which transmits only light at fluorescent wavelengths is installed in front of the CCD camera 39.

An optical fiber 42 from an external illuminating device 41 is connected under the zoom lens 34 in the microscope 31. Illumination light L from the optical fiber 42 is guided to an irradiation hole 46 in the bottom surface of the microscope 31 through lenses 44 and a mirror 45 which are installed in an internal optical path 43 of the microscope 31. The resultant illumination light L can be irradiated downward onto an affected area T from the irradiation hole 46.

As a source of light, a xenon lamp 47 is installed in a housing 41 of an external illuminating device. A predetermined excitation filter 48 transmits only light at a necessary wavelength out of the illumination light L from the xenon lamp 47, and the light at the necessary wavelength is supplied to the microscope 31. The excitation filter 48 can slide upward and downward. Therefore, it can advance to, and withdraw from, the optical path from the xenon lamp 47. This excitation filter 48 is used to excite indocyanine green, and has a characteristic of transmitting only light with a wavelength of approximately 805 nm. Otherwise, the rotary plate 16 with the excitation filters 21 to 23 shown in FIG. 3 may be installed instead of the excitation filter 48.

In addition, it is desirable that a single transmitting optical filter (optical means) 49 is fixed to the irradiation hole 46 of the microscope 31. Because only the single optical filter 49 is fixed, the optical filter 49 can be fixed even to a narrow space in the irradiation hole 46. This optical filter 49 is a heat-radiation cutting filter. Specifically, the optical filter 49 has a characteristic of cutting out all the wavelengths longer than 810 nm as a threshold wavelength from the illumination light L from the xenon lamp 47.

Next, descriptions will be provided for how the second embodiment operates when indocyanine green is used as a fluorescent substance. The xenon lamp 40 irradiates the illumination light L, which has a radiation spectrum as shown in FIG. 8, as parallel rays. When the illumination light L irradiated from the microscope 1 passes the excitation filter 48, it has the wavelength at approximately 805 nm which is needed to excite indocyanini green.

Figure 9:
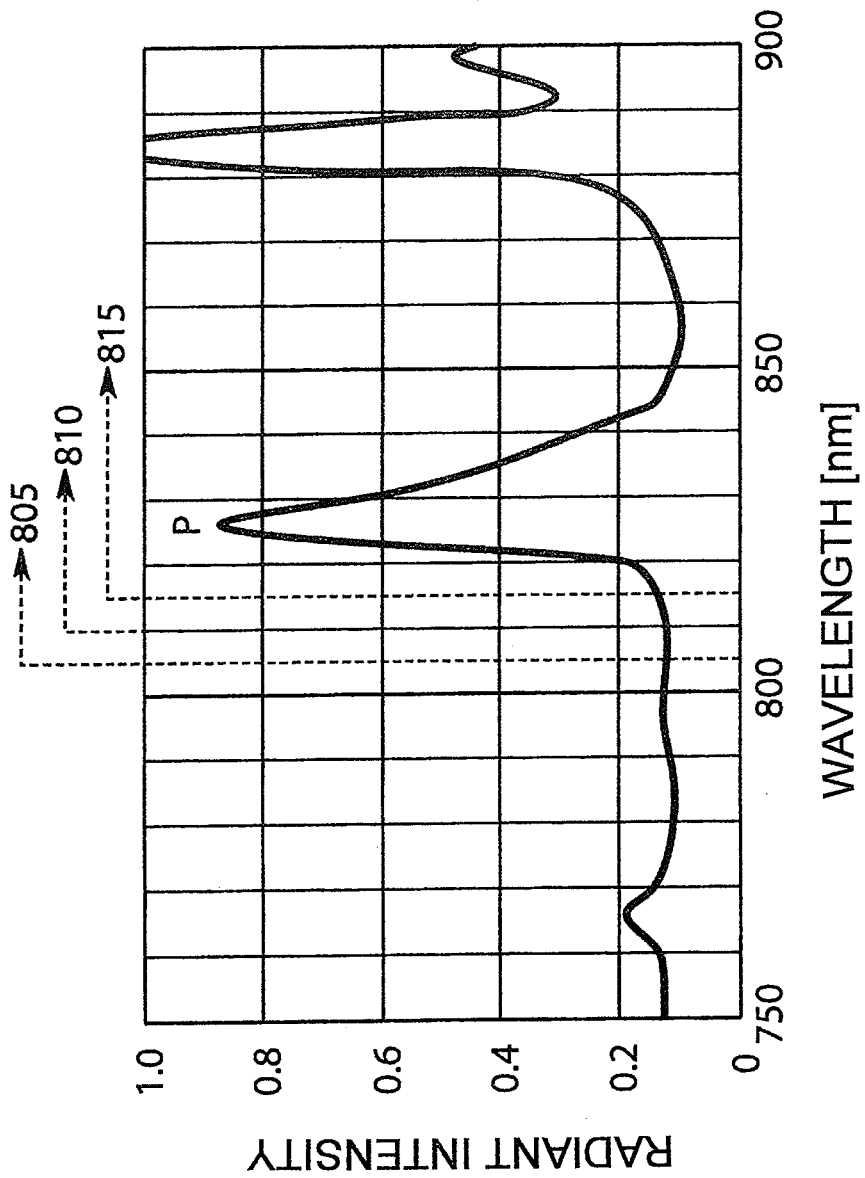
FIG. 9 is a graph showing a radiation spectrum of the xenon lamp at approximately a wavelength of 800 nm.

On the other hand, the optical filter 49, which is fixed to the irradiation hole 46 of the microscope 31, has a characteristic of cutting out all the wavelengths in the infrared region, which are longer than 810 nm (the threshold value), from the illumination light L, as clear from FIGS. 9 and 10 (magnifying a main part of FIG. 8). The optical filter 49 is always fixed on the optical path of the illumination light from the xenon lamp 47 to the affected area T through the microscope 31 (the irradiation hole 46), and is placed in order to cut out heat radiation components from the illumination flux L.

As a result, the wavelength of the illumination light L from the xenon lamp 47 is shorter than 810 nm, because the illumination light L has passed the excitation filter 48. Accordingly, the illumination light L is also transmitted in the optical filter 49 of the irradiation hole 46 as it is, and is thus irradiated onto the affected area T.

Indocyanine green as a fluorescent substance is beforehand accumulated in the affected area T. The 805-nm reflection light L for exciting indocyanine green causes emission of fluorescent light from the affected area T. The fluorescent light is introduced to the microscope 31 through the focus lenses 33. Part of the fluorescent light is split by the zoom splitter 38. Thereafter, an image represented by the split part of the fluorescent light is taken by the CCD camera 39 through the filter 40. When the thus-captured fluorescent image is displayed on a monitor (not illustrated), it is possible to observe the condition of the affected area T as the fluorescent image.

In this respect, even if the illumination light L is introduced into the microscope 31 in a full output mode as a result of the failure of the slide mechanism of the excitation filter 48 in the housing 41 and the resultant dislocation of the excitation filter 48 from the optical path from the xenon lamp 47, the affected area T is not overheated. That is because: the optical filter 49 is fixed to the irradiation hole 46 of the microscope 31; and the optical filter 49 cuts all the wavelengths longer than 810 nm, which become heat radiation. Particularly because the infrared region beyond the wavelength (810 nm) shorter than a wavelength (approximately 825 nm) which is substantially the first peak P of the radiant intensity of the xenon lamp 47, is cut out, it is possible to infallibly eliminate heat irradiation from the illumination light from the xenon lamp 47. Note that, even when a normal observation is carried out by use of the illumination light including visible light by intentionally removing the excitation filter 48, similarly, it is possible to infallible eliminate heat radiation. In other words, no heat radiation components are irradiated onto the affected area T from the opening portion 49 of the microscope, no matter which type of excitation filter may be selected, or whether or not any one of the excitation filters may be selected.

Even if another excitation filter is used inside the housing 41 when a fluorescent substance other than indocyanini green is used, light once transmitting in the excitation filter can be always transmitted in the optical filter 49 which is fixed to the microscope 31. In other words, even a fluorescent light from indocyanini green, whose excitation wavelength (approximately 805 nm) is the closest to the infrared wavelengths, can be transmitted in the optical filter 49. For this reason, light for exciting a fluorescent substance other than indocyanine green can be transmitted in the optical filter 49 as well.

The microscope 31 according to this embodiment can be applied to the microscope 4 according to the first embodiment which is shown in FIG. 1. Specifically, the stand device 1 is connected to the microscope 31, and the illumination light L from the light generating unit 6 passes the internal optical path 43. The infrared region of the illumination light L is cut out by the optical filter 49, and the resultant light is finally irradiated onto the affected area T.

In the foregoing embodiment, the transmitting optical filter 49 has been shown as an instance of the optical means. However, a reflecting optical filter, a combination of the transmitting optical filter and the reflecting optical filter, or any other optical means may be used. In addition, the present invention can be applied to illumination light from a different source of light (for instance, a halogen lamp).

(Third Embodiment)

Figure 16:
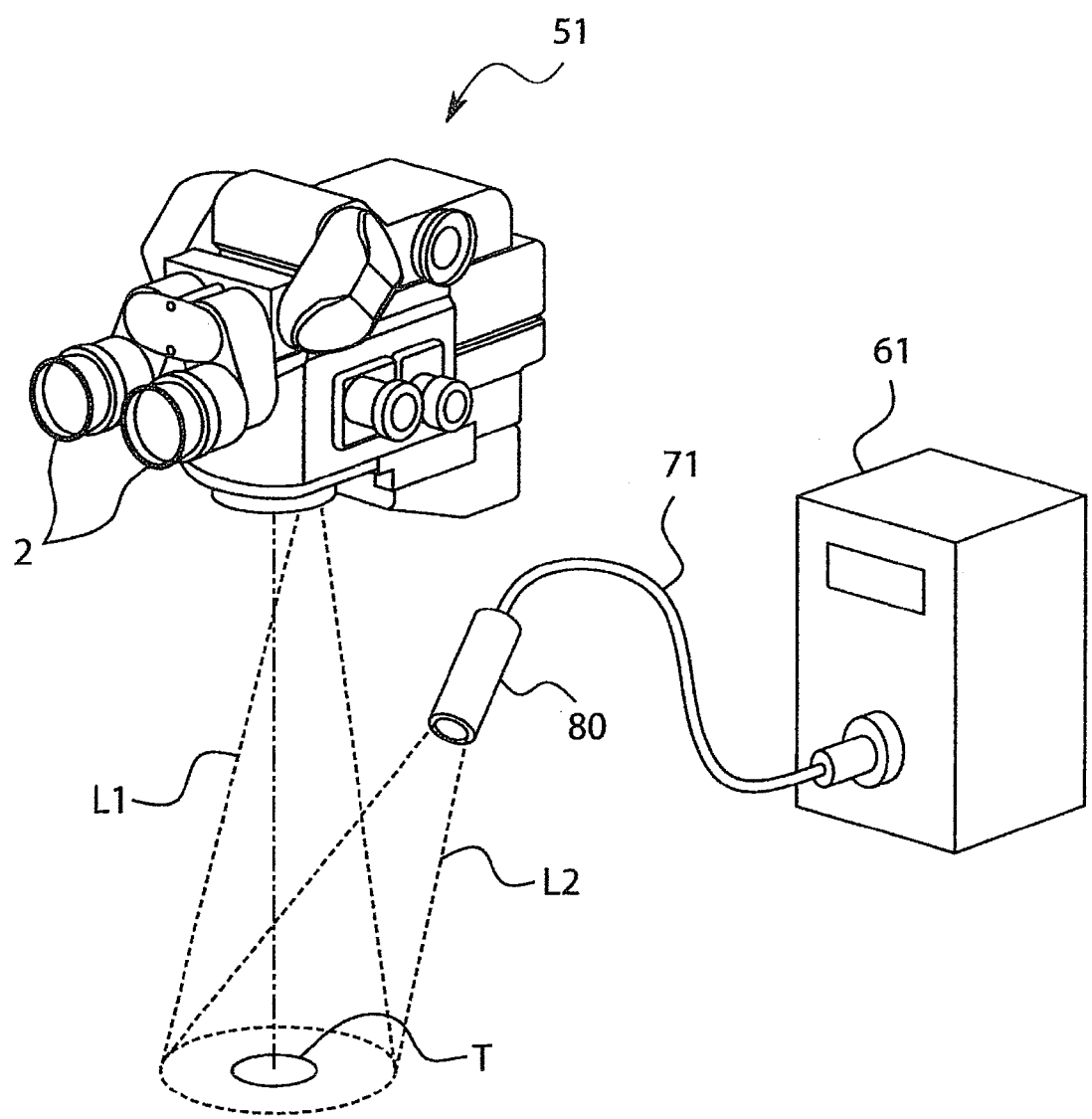
FIG. 16 is an overall perspective view showing a microscope and an external illuminating device according to a third embodiment of the present invention.
Figure 17:
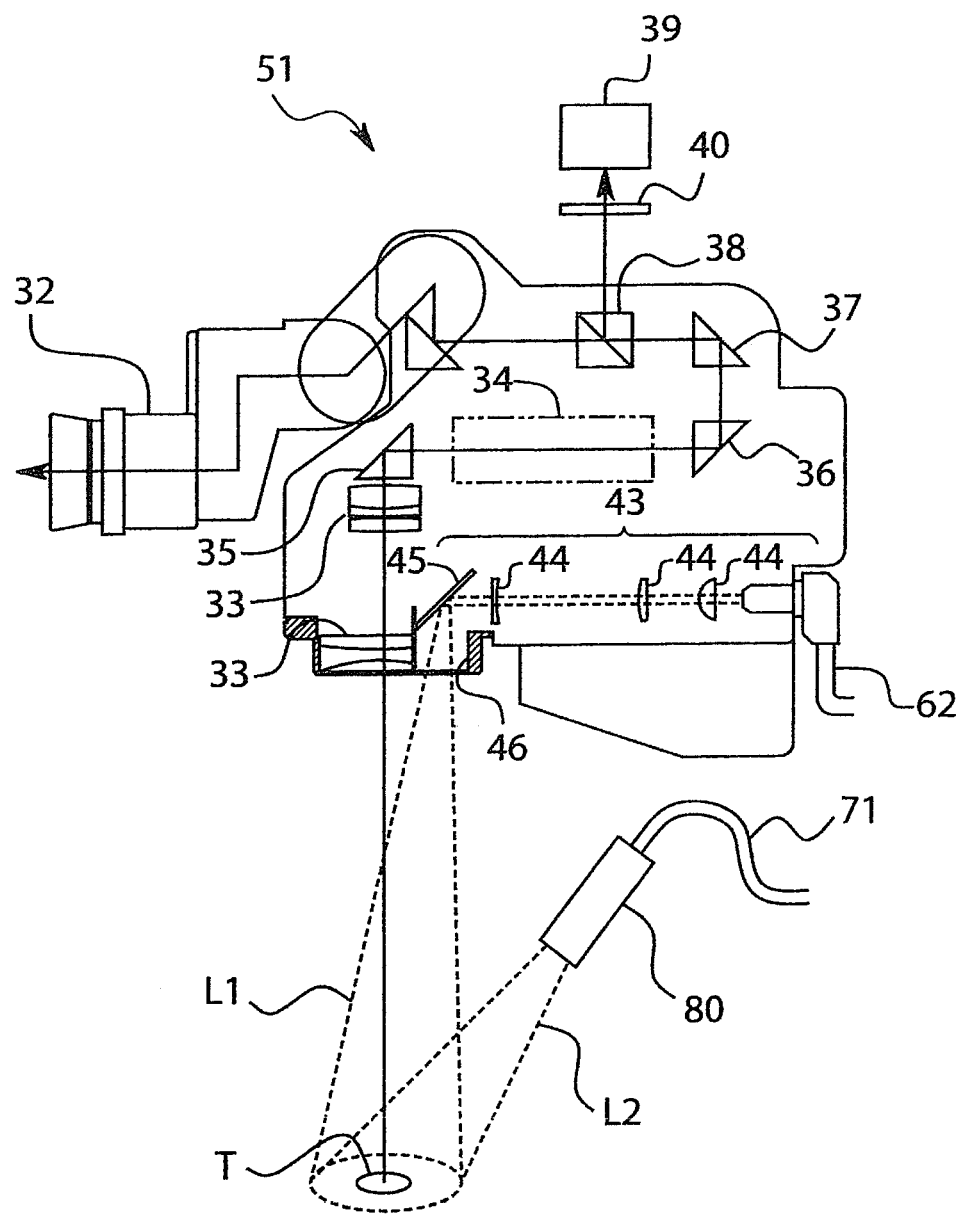
FIG. 17 is a schematic view showing an internal configuration of the microscope according to the third embodiment of the present invention.

FIGS. 16 to 20 are diagrams showing a third embodiment of the present invention. As described later, when an affected area is observed by use of a microscope 51, the present embodiment illuminates the affected area. As shown in FIG. 17, the configuration of the microscope 51 for a surgical operation according to the third embodiment is similar to the configuration of the microscope 31 according to the second embodiment. The configuration of the microscope 51 is different from the configuration of the microscope 31 only in that the configuration of the microscope 51 includes no optical filter 49 shown in FIG. 13. Accordingly, descriptions for the optical system will be omitted. The microscope 51 shown in FIG. 16 is supported by an arm of the stand device (see FIG. 1), for instance, inside an operating room as in the case of the microscope 4 which has been described with regard to the first embodiment.

As shown in FIG. 17, an optical fiber 62 (for instance, the optical fiber 5 shown in F*ig*.3) from a light generating unit installed in a stand device (for instance, the stand device 1 shown in FIG. 1) is connected under a zoom lens 34 of a microscope 51. Illumination light L from the optical fiber 62 is introduced to an irradiation hole 46 in the bottom surface of the microscope 51 through lenses 44 and a minor 45 which are placed in an optical path 43 inside the microscope 51, and can be irradiated onto an affected area T through the irradiation hole 46. Note that the illumination light L according to this embodiment includes only visible light components but no infrared light components.

Figure 18:
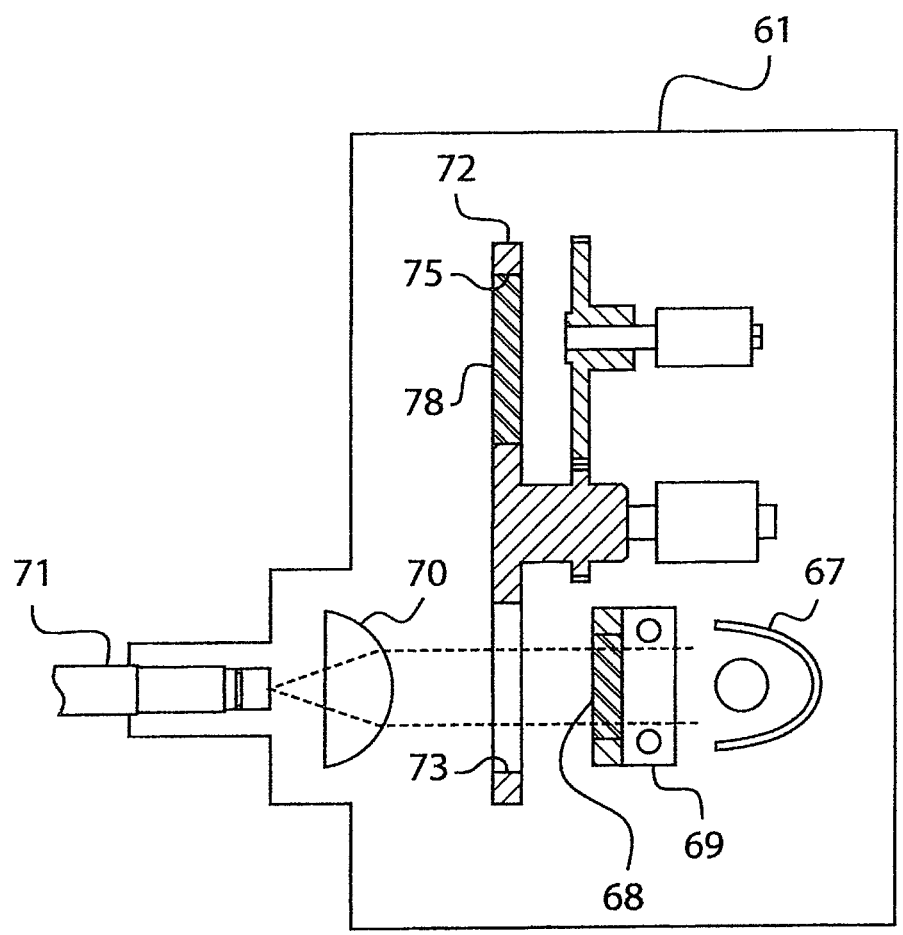
FIG. 18 is a schematic view showing an internal configuration of an external illuminating device according to the third embodiment.
Figure 19:
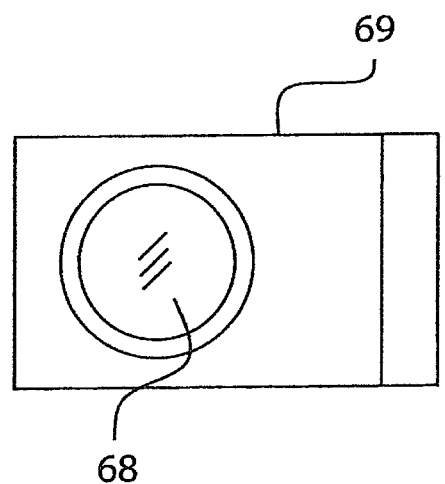
FIG. 19 is a plan view showing an optical filter according to the third embodiment.

As shown in FIG. 18, a xenon lamp 67 as a source of light is installed in a housing 61 of an external illuminating device. A transmitting optical filter (optical means) 68 is fixed by use of a fixation plate 69 in front of the xenon lamp 67 (see FIG. 19). It is desirable that the optical filter 68 be installed singularly. In this case, the installation can be achieved by use of an interstitial space in the conventional external illuminating device.

Figure 20:
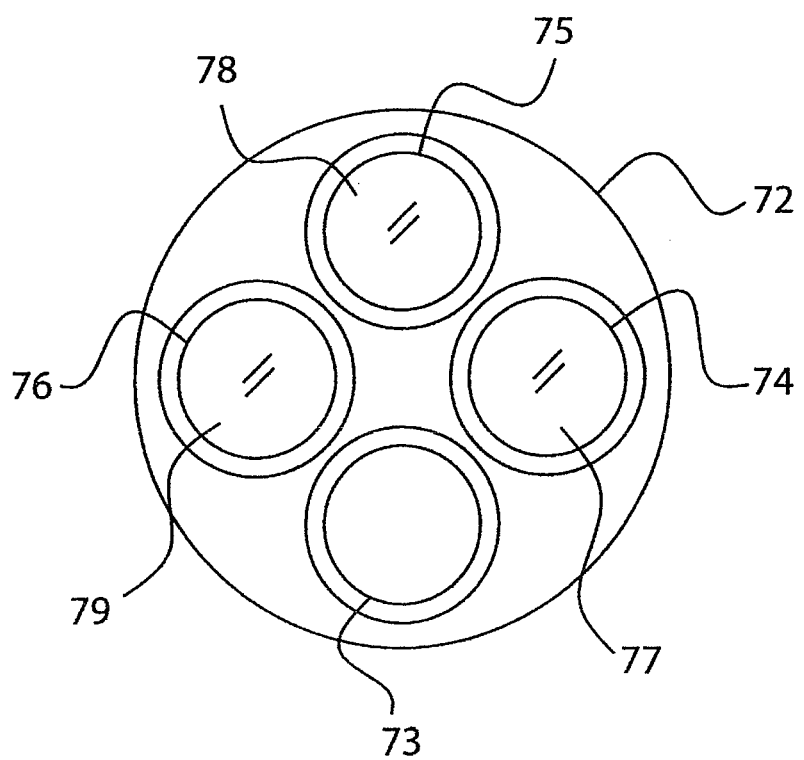
FIG. 20 is a plan view showing a rotary plate according to the third embodiment.

A condenser lens 70 is installed in front of the optical filter 68. The base end of an optical fiber 71 is fixed to a light-collecting point of the condenser lens 70. A rotary plate 72 shown in FIG. 20 is installed between the optical filter 78 and the condenser lens 70. Four holes 73 to 76 are formed in the rotary plate 72. One hole 73 is opened, and the 3 other holes are respectively provided with a first excitation filter 77, a second excitation filter 78 and a third excitation filter 79. The first to third excitation filters are bandpass filters for selectively transmitting light at necessary wavelengths depending on a fluorescent substance.

A front end of the optical fiber 71 is provided with an irradiation unit 80. Illumination light L2 can be irradiated onto the affected area T from this irradiation unit 80.

Next, descriptions will be provided for how the third embodiment operates when indocyanine green is used as a fluorescent substance. The xenon lamp 67 irradiates the illumination light L2, which has a radiation spectrum as shown in FIG. 8, as parallel rays. The threshold value of the fixed optical filter 68 is set at 810 nm, as clear from FIGS. 9 and 10 (magnifying the main part of FIG. 8). Thus, the optical filter 68 has a characteristic of cutting out all the wavelengths in the infrared region, which are longer than 810 nm, from the illumination light L2. When indocyanine green is used, the hole 73 penetrating the rotary plate 72 is positioned by revolving in order to face to the optical filter 68.

Accordingly, as shown in FIG. 10, the illumination light L2 from the xenon lamp 67 turns into light from which all the wavelengths in the infrared region, which are longer than the wavelength of 810 nm, are cut out from the illumination light. The resultant light passes the hole 73 penetrating the rotary plate 72, and is condensed by the condenser lens 70. Thereafter, the condensed light is irradiated onto the affected area T through the optical fiber 71. When the illumination light L2 is irradiated from the external illuminating device, no illumination light L1 is irradiated from the microscope 51. This illumination light L1 is used when a normal observation but not a fluorescence observation is carried out.

Indocyanine green is beforehand accumulated in the affected area T. The illumination light L2, which includes a 805-nm wavelength for exciting indocyanine green, causes emission of fluorescent light from the affected area T. The fluorescent light is introduced into the microscope 51 from the focus lenses 3. Part of the fluorescent light is split by the beam splitter 38. Thereafter, an image represented by the split part of the fluorescent light is taken by a CCD camera 39 through a filter 40. When the thus-taken fluorescent image is displayed on a monitor (not illustrated), it is possible to observe the condition of the affected area T as the fluorescent image.

Although the illumination light L2 is irradiated onto the affected area T, the affected area T is not overheated. That is because the illumination light L2 includes no wavelengths in the infrared region, which are longer than 810 nm, and which become heat radiation. Particularly because the infrared region beyond the wavelength (810 nm) shorter than 825 nm, which is substantially the first peak P of the radiant intensity of the xenon lamp 67, is cut out, it is possible to infallibly eliminate heat radiation from the illumination light from the xenon lamp 67.

When a fluorescent substance other than indocyanine green is used, light at a wavelength needed to excite the fluorescent substance may be selectively transmitted by use of a corresponding one of the first to third excitation filters 77 to 79 in the rotary plate 72 (see FIG. 20), which is other than the optical filter 68. In this case, the optical filter 68 can infallibly deal with 5-aminolevulinic acid and talaporfin sodium whose excitation wavelengths are shorter than that of indocyanine green, no matter which type of excitation filter may be selected, or whether or not any one of the excitation filters may be selected. That is because the optical filter 68 has the characteristic in which the optical filter 68 is capable of dealing with even indocyanine green whose excitation wavelength is the closest to the infrared wavelengths.

When any other fluorescent substance is used, heat radiation components can be infallibly eliminated from the illumination light L2 from the xenon lamp 67. That is because the optical filter 68, which is configured to cut out the infrared region beyond a wavelength shorter than the wavelength which is the first peak P of the radiant intensity of the illumination light from the xenon lamp 67, is fixed inside the housing 61 of the external illuminating device. In other words, no heat irradiation components are irradiated onto the affected area T, no matter which type of excitation filter may be selected, or whether or not any one of the excitation filters may be selected. That is because: the optical filter 68 is always fixed on the optical path of the illumination light from the xenon lamp 67 to the irradiation unit 80; and the optical filter 68 is placed in order to cut out the heat radiation components from the illumination flux L2.

The transmitting optical filter 68 has been shown as an instance of the optical means according to this embodiment. Note that, however, a reflecting optical filter, a combination of the transmitting optical filter and the reflecting optical filter, or any other optical means may be used.

Instead of the xenon lamp, a halogen lamp capable of exciting the above-mentioned fluorescent substances may be used as the source of light for the illumination light L2. Although illumination light from the halogen lamp includes infrared light, such infrared light is always cut out by the optical filter 68 as well. For this reason, it is possible to prevent the affected area from being heated.

Industrial Applicability

When a fluorescence observation is applied to an affected area during a surgical operation, the optical filter is capable of: infallibly eliminate heat radiation of the infrared region from the illumination light; and accordingly preventing the affected area from being heated (for instance, from suffering from a burn and the like).

The invention claimed is:

1. A medical stand device comprising:
an arm configured to support a microscope; a stand main body configured to support the arm;
a light generating unit installed inside the stand main body, the light generating unit including a xenon lamp as a light source, and being configured to generate illumination light using the xenon lamp, which is supplied to the microscope; and
optical means configured to cut out the illumination light having a wavelength of a peak or longer in an emission spectrum of the xenon lamp, the peak substantially firstly appearing as infrared light on a visible light side of an infrared region in the emission spectrum and configured to transmit or reflect the illumination light including a wavelength of excitation light of an indocyanine green or shorter, by cutting out the illumination light having wavelengths longer than a threshold wavelength, the threshold wavelength being longer than 805 nm and shorter than 815 nm, wherein
the optical means is fixed on an optical path of the illumination light from the light generating unit to the microscope.

2. The medical stand device according to claim 1, further comprising an optical fiber configured to transmit the illumination light, wherein the optical fiber is installed in at least part of the optical path.

3. A medical microscope comprising:
a microscope main body;
an internal optical path provided in the microscope main body, and configured to transmit illumination light from a xenon lamp, the illumination light being introduced from outside an irradiation hole formed in a bottom surface of the microscope main body, the bottom surface facing an affected area, and the illumination light going out of the irradiation hole after passing the internal optical path; and
optical means configured to cut out the illumination light having a wavelength of a peak or longer in an emission spectrum of the xenon lamp, the peak substantially firstly appearing as infrared light on a visible light side of an infrared region in the emission spectrum, and configured to transmit or reflect the illumination light including a wavelength of excitation light of an indocyanine green or shorter, by cutting out the illumination light wavelengths longer than a threshold wavelength, the threshold wavelength being longer than 805 nm and shorter than 815 nm, wherein the optical means is fixed to any one of the internal optical path and the irradiation hole.

4. The medical microscope according to claim 3, further comprising:

an arm configured to support the microscope main body;

a stand main body configured to support the arm; and a light generating unit installed inside the stand main body, including the xenon lamp as a light source, and configured to generate the illumination light using the xenon lamp and to supply the illumination light to the microscope main body.

5. An external illuminating device configured to illuminate an affected area through an irradiation hole of a medical microscope, the affected area being to be observed by use of the medical microscope, comprising:

a xenon lamp for an illumination light;

a housing configured to house the xenon lamp;

optical means configured to cut out the illumination light having a wavelength of a peak or longer in an emission spectrum of the xenon lamp, the peak substantially firstly appearing as infrared light on a visible light side of an infrared region in the emission spectrum and configured to transmit or reflect the illumination light including a wavelength of excitation light of an indocyanine green or shorter, by cutting out the illumination light having wavelengths longer than a threshold wavelength, the threshold wavelength being longer than 805 nm and shorter than 815 nm, wherein the light source is any one of a xenon lamp and a halogen lamp, and the optical means is placed in an optical path of the illumination light inside the housing.

6. The external illuminating device according to claim 5, further comprising:

an optical fiber connected to the housing, and configured to transmit the illumination light.

\* \* \* \* \*